United States Patent [19]
Fedorov et al.

[11] Patent Number: 5,846,950
[45] Date of Patent: Dec. 8, 1998

[54] PHARMACEUTICAL COMPOSITION FOR PROMOTING THE PROLIFERATION OF HUMAN CORNEAL ENDOTHELIUM AND A METHOD FOR USING THEREOF

[75] Inventors: Svyatoslav Nikolaevich Fedorov; Tamara Iliinichna Ronkina; Andrei Valentinovich Zolotarevsky; Sergei Nikolaevich Bagrov; Sergei Viktorovich Novikov; Evgeny Viktorovich Larionov, all of Moscow, Russian Federation

[73] Assignee: Mezhotraslevoi Nauchno-Tekhnichesky Komplex "Mikrokhirurgia Glaza", Moscow, Russian Federation

[21] Appl. No.: 742,748

[22] Filed: Nov. 1, 1996

[30] Foreign Application Priority Data

Nov. 6, 1995 [RU] Russian Federation ............. 95118911

[51] Int. Cl.⁶ ........................ A61K 31/715; A61K 31/725
[52] U.S. Cl. ................................ 514/53; 514/56; 514/912
[58] Field of Search ................................ 514/53, 56, 912

[56] References Cited

PUBLICATIONS

Experimental Eye Research, vol. 45, No. 6, N. Landshman et al, Dec. 1987.

*Primary Examiner*—Zohreh Fay
*Attorney, Agent, or Firm*—Jacobson, Price, Holman & Stern, PLLC

[57] ABSTRACT

A pharmaceutical composition for promoting the proliferation of human corneal endothelium comprising:

1 ml of 0.15M phosphate buffer, at pH 7.4;

400–800 $\mu$g of heparin;

1.0–5.0 $\mu$g of $Cu^{2+}$;

37.5–375 $\mu$g of /3-0-b-D-gelactopyranosyl-(1-4)-0-(2-acetamido-b-D-glucopyranosyl-6-sulfate)-1/as the salt of a basic metal; and 12.5–125 $\mu$g of copolymer (b-gucuronic acid (1–3)-N-acetyl-b-galactosamino-4-(or 6-) -sulfate-(1–4) as the salt of a basic metal. Such a composition is particularly useful for promoting the proliferation of human corneal endothelium in conditions associated with cataract extraction followed by artificial lens implantation, wherein the composition is injected into the patient's anterior eye chamber in an amount of between 0.2–02.25 ml, immediately after performing the operation. In all other cases, the pharmaceutical composition is injected into a patient's anterior eye chamber by phonophoresis in a continuous mode, at intensity 0.1–0.3 $V/cm^2$ for 10 minutes, with the composition used in the amount of 5 ml daily for 4–6 days.

5 Claims, No Drawings

PHARMACEUTICAL COMPOSITION FOR PROMOTING THE PROLIFERATION OF HUMAN CORNEAL ENDOTHELIUM AND A METHOD FOR USING THEREOF

FIELD OF THE INVENTION

This invention relates to the art of medicine and, more particularly, the invention relates to ophtalmology

BACKGROUND OF THE INVENTION

The potential of mitotic division of human corneal endothelium is well known to be very limited. The endothelial tissue regeneration is generally associated with hypertrophy, subsequent increase the occupied area and motility of endothelial cells. If the density of endothelial cells decreases below the critical level (less than 100 cells/mm$^2$), corneal endothelial-epithelial tissue distrophy may occur.

A method for regenerating the damaged corneal endothelium under promoting its mitotic division has been known, wherein the purified fibroblast heparin-containing growth factor is injected to the anterior chamber of the eye.

However, the positive effects has been obtained only in experiments on cats (Exp. Eye Res., 1987, vol. 45, pp. 805–811).

In addition, this method needs the use of a substance to be injected to the eye chamber, which should be protein in nature, because fibroblast growth factor is a polypeptide that may cause allergic reactions.

Thus, there is an urgent need to provide a safety and efficient pharmaceutical composition and a method for regenerating the damaged human corneal endothelium.

SUMMARY OF THE INVENTION

It is the main object of the present invention to provide a pharmaceutical composition which makes it possible to promote the corneal endothelial tissue proliferation, increase the motility of endothelial cells, activate the exchange in corneal connective tissue and inhibit the progression of corneal inflammations.

Another object of the present invention is to provide a safety pharmaceutical composition that does not cause any allergic reactions.

Finally, it is an object of the present invention to provide an effective method for promoting the proliferation of human corneal endothelium.

The main and other objects of the present invention are accomplished by that a pharmaceutical composition for promoting the proliferation of human corneal endothelium includes the following ingredients: 1 ml of 0,15M phosphate buffer, at pH 7,4; 400–800 µg of heparin; 1.0–5.0 µg of Cu$^{2+}$; 37.5–375 µg of -3-0-b-D-galactopyranosyl-(1–4)-0-(2-acetamido-b-D-glucopyranosyl-6-sulfate)-1/as the salt of a basic metal chosen from the group consisting of potassium or sodium; 12.5–125 µg of copolymer (b-glucoronic acid (1–3)-N-acetyl-b-galactosamino-4-(or 6)- sulfate-(1–4) as the salt of a basic metal chosen from the group consisting of potassium or sodium The proposed pharmaceutical composition provides the promotion of corneal endothelial tissue proliferation, the increase in motility of endothelial cells, the activation of corneal connective tissue exchange and the inhibition of developing the corneal inflammations.

In accordance with the main and other objects, the invention further resides in that a method for promoting the proliferation of human corneal endothelium in conditions associated with cataract extraction followed by artificial lens implantation comprises injecting the proposed pharmaceutical composition into the patient's anterior eye chamber in the amount of 0.2–0.25 ml after completion of operation for cataract extraction with an artificial lens implantation.

Another aspect of the invention resides in that at the initial stage of corneal endothelial-epithelial distrophy for preventing its progression in postoperative period in conditions associated with keropathy and decreasing the density of endothelial cells in patients with artificial lens, the method, according to the invention, comprises injecting the proposed pharmaceutical composition into to the patient's anterior eye chamber by phonophoresis in a continuous mode at intensity 0.2–0.3 V/cm$^2$ for 10 minutes, with the composition used in the amount of 5 ml and the procedure carried out daily for 4–6 days.

A method of the present invention makes it possible to promote effectively the proliferation of human corneal endothelium, activate the exchange in corneal connecting tissue and inhibit the development of corneal inflammations.

DETAILED DESCRIPTION OF THE INVENTION

A pharmaceutical composition of the present invention is a solution containing a mixture of 0.15M phosphate buffer (pH 7,4), which includes the following substances belonging to a class of mucopolysaccharides of polysulfuric acid: heparin [Sodium or potassium 4-0-a-L-idopyranosyl-2sulfate-(1-4)0-(2-deoxy-2-sulfamido-d-D-glucopyranosyle-6-sulfate)-(1-4)-0-b-D-lucopyranurasynol-(1–4)-0-(2-deoxy-2-sulfamido-b-D-glucopyranosyl) salt], has a relative molecular weight of about 16,000. In the proposed composition the concentration of heparin is of 400 to 800 µg/l ml phosphate buffer. copolymer, sodium or potassium salt of b-glucuronic acid (1–3)-N-acetyl-b-galactosamino-4-(or 6)-sulfate (1–4) (chondroitin sulfate). The concentration of chondroitin sulfate in the pharmaceutical composition of the invention is of 37.5 to 375 µg/l ml phosphate buffer. sodium or potassium /-3)-0-b-D-galactopyranosyl-(1–4)-0-(2-acetamido-b-D-glucopyranosyl-6-sulfate)-1/salt (keratin) sulfate). In the proposed composition the concentration of keratan sulfate is of 12.5–125 µg/l ml phosphate buffer.

The concentrations of ingredients of the composition, chosen within the specified limit ranges provides the attainment of the desired results. The decrease of their concentrations below the specified lower limit range leads to a decrease in efficiency of the composition; the increase of the concentrations of ingredients in question above the specified upper limit range results in side-effects occurring; and a decrease in the efficiency of the composition.

The pharmaceutical composition of the invention can be prepared in the following way. First, the heparin Cu$^{2+}$ complex is prepared. To this end, to 5 ml of a heparin solution (heparin for injections, 5000 U/ml=345 mg/ml) 10 ml of 0.1M tris-HCl buffer, pH 7.5, and 30 mg CuSO$_4$ . 5H$_2$O are added, the resultant mixture is stirred and allowed to stand at 4° C. for 12 hours.

The heparin-Cu$^{2+}$complex is isolated by gelchromatography. As a result of chromatographic isolation, in 1 ml of eluant there was contained 400 U of heparin, that equal to 3.6 mg of heparin and 0.4 mg of Cu$^{2+}$.

The resultant solution containing such complex is combined with 0.15M phosphate buffer at pH 7.4 and heparin solution such that concentrations of heparin and Cu$^{2+}$ions were 400–800 μg and 1.0–5.0 4 μg, respectively, in 1 ml 0.15M phosphate. 0.15M phosphate buffer includes: sodium chloride 0.85 g, monosodium salt 0.005 g, disodium salt 0.06 g, water 100 ml. To the resultant composition there are added 37.5–375 μg of ceratan sulfate and 12.5–125 μg of chondroitin sulfate.

The pharmaceutical composition of the present invention may be used immediately after completing the operation for cataract extraction with implantation of artificial lens, in early postoperative period in conditions associated with keropathy, at early endothelial-epithelial distrophy (at 1–2 stage of disease development) as well as to decrease the density of endothelial cells and danger of occurring endothelial-epithelial distrophy in patients whose had been operated for cataract extraction followed by artificial lens implantation.

For a better understanding the present invention the following Examples are given to illustrate a method of the treatment with using the proposed pharmaceutical composition.

EXAMPLE 1

Patient S. Diagnosis: immature senile cataract. The density of endothelial cells was 2200–2300 cells/mm$^2$. The routine extracapsular cataract extraction followed by implantation of an artificial lens was carried out without any complications.

Immediately after performing the operation, 0.2 ml of a solution of the proposed pharmaceutical composition was injected into the anterior eye chamber at the following mixture ratio (based on 1 ml 0.15M phosphate buffer, pH=7,4): Cu$^{2+}$1.0 μg; sodium-ceratan sulfate 37.5 μg and chondroitin sulfate 12.5 μg.

Four months after making the operation, the density of endothelial cells was 2150–2220 cells mm$^2$. The loss of endothelial cells was 2.9%.

EXAMPLE 2

Patient A. Diagnosis: immature senile cataract. The density of endothelial cells of 2200–2400 cells/mm$^2$. The routine extracapsular cataract extraction followed by implantation of an artificial lens was carried out.

The operation was finished with injecting 0.25 ml of a solution of the proposed pharmaceutical composition into the anterior eye chamber at the following mixture ratio (based on 1 ml 0.15M phosphate buffer, pH=7,4): potassium-heparin 600 μg, Cu$^{2+}$μg; potassium-ceratan sulfate 150 μg and potassium-chondroitin sulfate 150 μg.

Five months after making the operation the density of endothelial cells was 2100–2300 cells/mm$^2$. The loss of endothelial cells was 4%.

EXAMPLE 3

Patient M. Diagnosis: the right eye: there is aphakia. The iris-immobilized intraocular lens was implanted in 1980. The endothelicyte density decreased gradually to the level of 1200–1300 cells/mm$^2$. The left eye: there are aphakia and endothelial-epithelial distrophy. The patient underwent the course of phonophoretic therapy with using the pharmaceutical composition of the present invention at the following mixture ratio (based on 1 ml 0.15M phosphate buffer, pH=7,4): potassium-heparin sulfate 800 μg; Cu$^{2+}$5 4μg; potassium-ceratan sulfate 375 μg and potassium-chondroitin sulfate 125 μg. After taking the course of treatment, no clinical symptoms have been noted against the left eye. Four months after treatment the endothelicyte density was of 1300–1450 cells/mm$^2$.

We claim:

1. A pharmaceutical composition for promoting the proliferation of human corneal endothelium comprising:

1 ml of 0.15M phosphate buffer, at pH 7.4;

400–800 μg of heparin;

1.0–5.0 μg of Cu$^{2+}$;

37.5–375 μg of /3-0-b-D-gelactopyranosyl-(1–4)-0-(2-acetamido-b-D-glucopyranosyl-6-sulfate)-1/as the salt of a basic metal; and 12.5–125 μg of copolymer (b-gucuronic acid (1–3)-N-acetyl-b-galactosamino-4-(or 6-)-sulfate-(1–4) as the salt of a basic metal.

2. A method for promoting proliferation of corneal endothelium, in a human patient, in conditions of cataract extraction followed by artificial lens implantation, comprising, immediately after cataract extraction with artificial lens implantation, injecting between 0.2–0.25 ml of a composition according to claim 1 into the eye of the human patient.

3. The method according to claim 2 wherein the composition is injected into the anterior chamber of the eye.

4. A method for promoting the proliferation of corneal endothelium, in a patient in need thereof, comprising injecting about 5 mls of the composition according to claim 1, into the eye of the patient, by phonophoresis in a continuous mode at an intensity of 0.2–0.3 V/cm$^2$, for approximately 10 minutes, daily for about 4–6 days.

5. The method of claim 4 wherein the method is useful at an initial stage of corneal endothelial-epithelial distrophy, for preventing the possibility of development thereof in a postoperative stage under keropathy and in case of decreasing the density of endothelial cells in a patient who has undergone cataract extraction with artificial lens implantation.

* * * * *